United States Patent [19]

Zerhouni et al.

[11] Patent Number: 4,953,554
[45] Date of Patent: Sep. 4, 1990

[54] MAGNETIC RESONANCE IMAGING METHOD

[75] Inventors: Elias Zerhouni, Baltimore, Md.; David M. Parish, Palo Alto, Calif.

[73] Assignees: Resonex, Inc., Sunnyvale, Calif.; Johns Hopkins University, Baltimore, Mass.

[21] Appl. No.: 164,263

[22] Filed: Mar. 4, 1988

[51] Int. Cl.⁵ .......................................... A61B 5/055
[52] U.S. Cl. .................................... 128/653 A
[58] Field of Search ................. 128/653; 324/306, 309

[56] References Cited

U.S. PATENT DOCUMENTS

| | | | |
|---|---|---|---|
| 4,382,184 | 5/1983 | Wernikoff | 128/653 |
| 4,520,828 | 6/1985 | Burl et al. | 128/653 |
| 4,528,985 | 7/1985 | Macovski | 128/653 |
| 4,532,473 | 7/1985 | Wehrli | 128/653 |
| 4,574,239 | 3/1986 | Singer | 128/653 |
| 4,625,169 | 11/1986 | Wedeen et al. | 324/309 |
| 4,782,839 | 11/1988 | Hennig et al. | 128/653 |

*Primary Examiner*—Ruth S. Smith
*Assistant Examiner*—John D. Zele
*Attorney, Agent, or Firm*—Flehr, Hohbach, Test, Albritton & Herbert

[57] ABSTRACT

A magnetic resonance imaging (MRI) method imposes void planes on tissue to be imaged, which may form a grid pattern of lines which, when later imaged, produces a reference void in the image. This is especially useful in studies of the heart where the contraction and relaxation of the heart can thus be measured. Also for static tissue the method is useful for radiation therapy port planning. The grid reference or void planes are formed by a simple use of an RF pulse in conjunction with the use of a slice select gradient which provides sufficient power so that those protons in the grid are saturated so that in the later imaging step there will be significant spin echo signal difference between the grid imposed areas and the remaining regions of the tissue.

9 Claims, 7 Drawing Sheets

FIG.—1

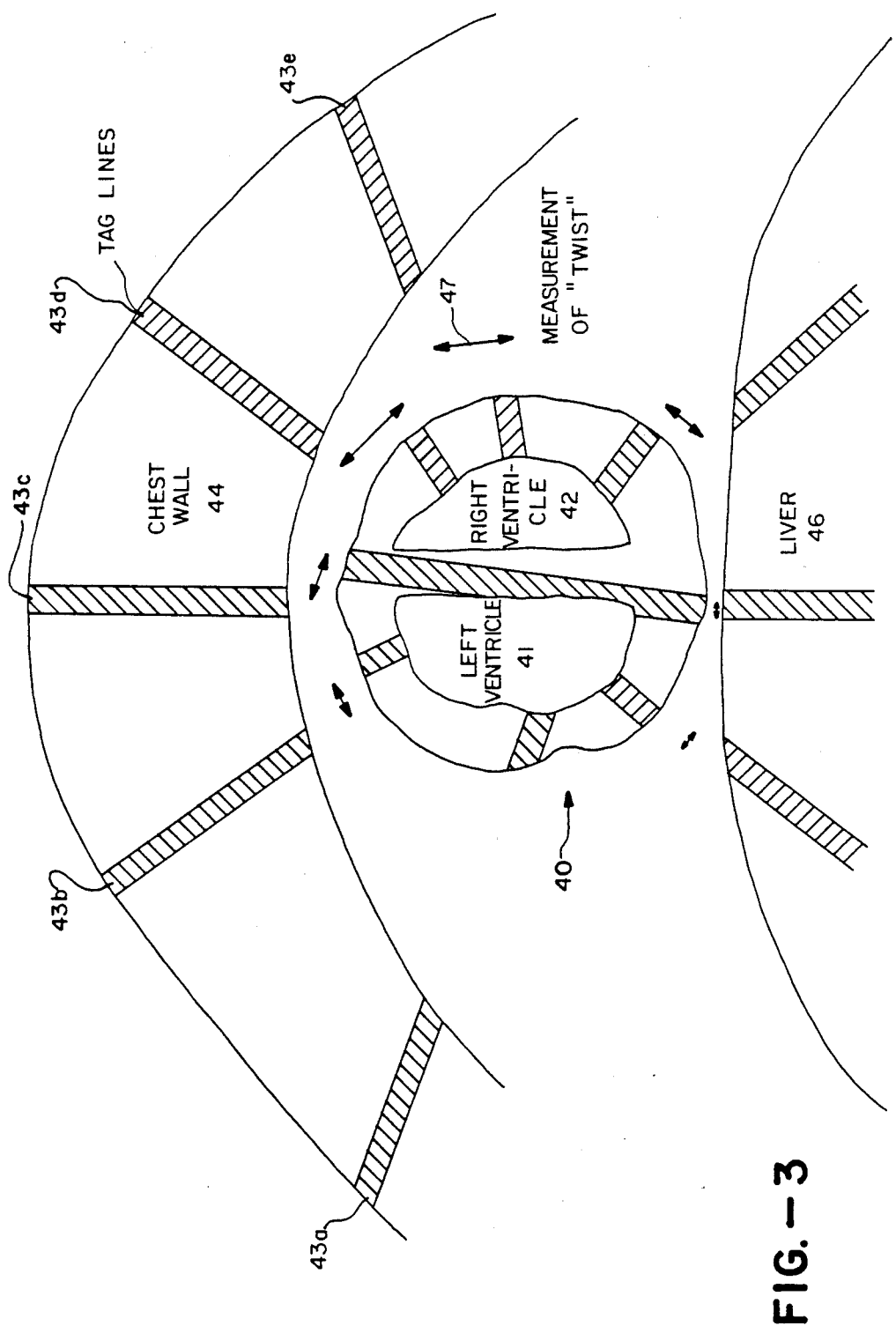
FIG.—3

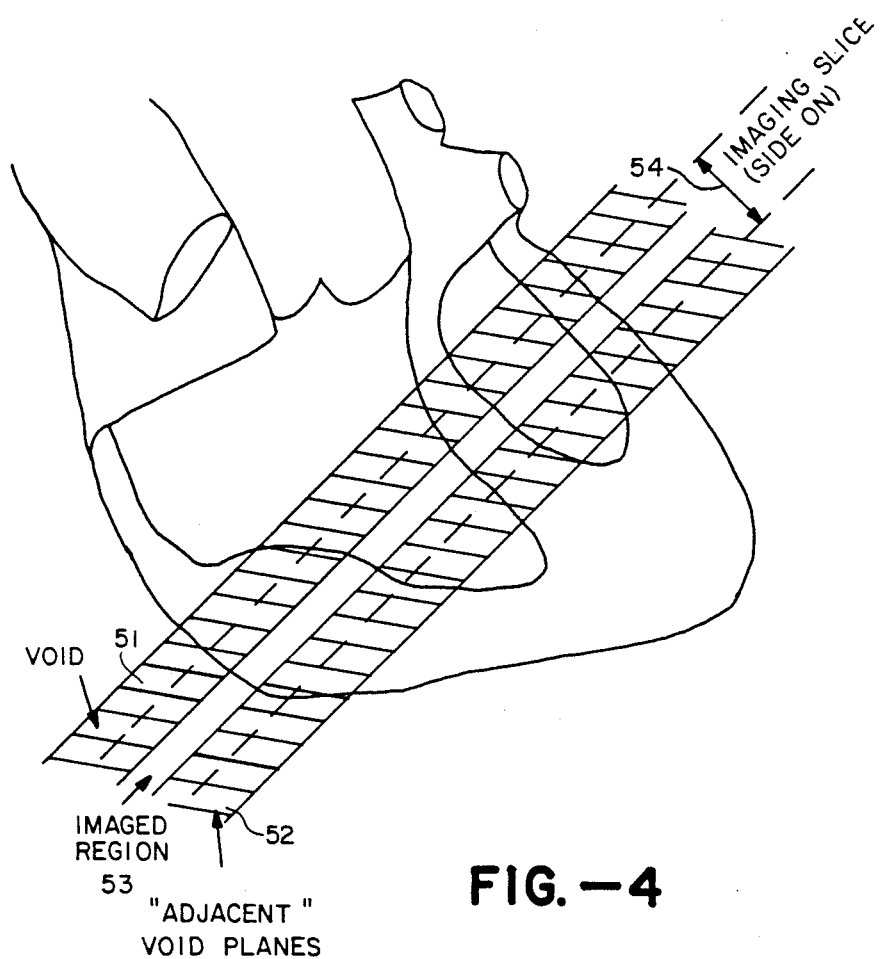
FIG.—4
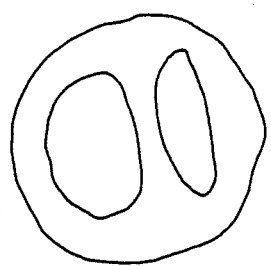
FIG.—4A

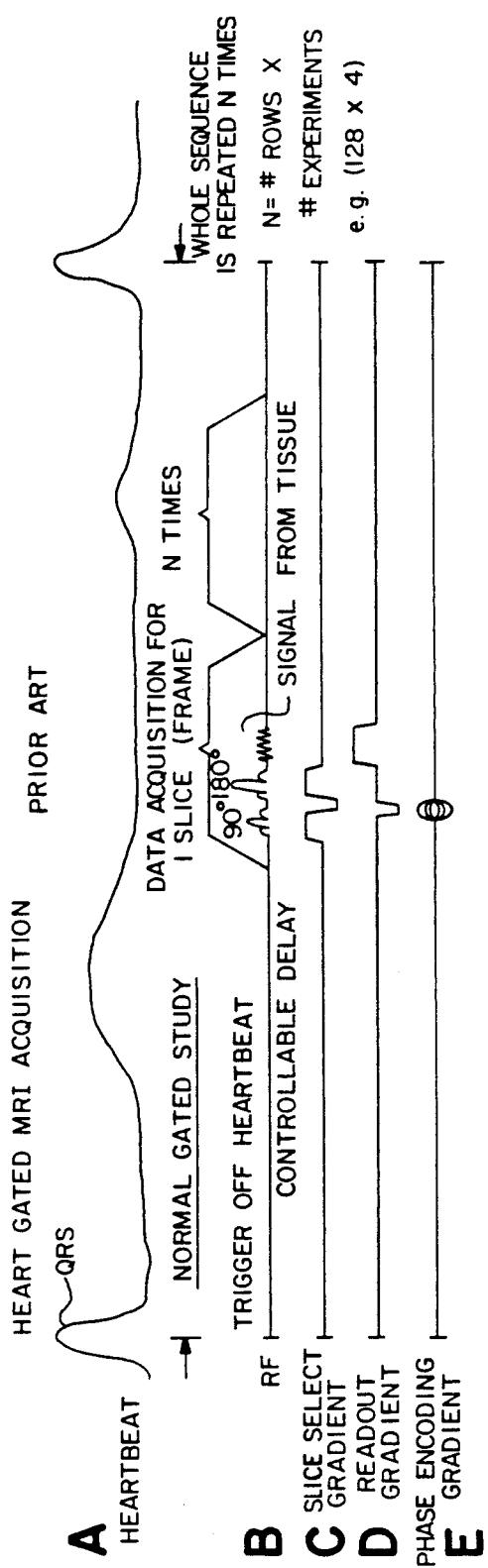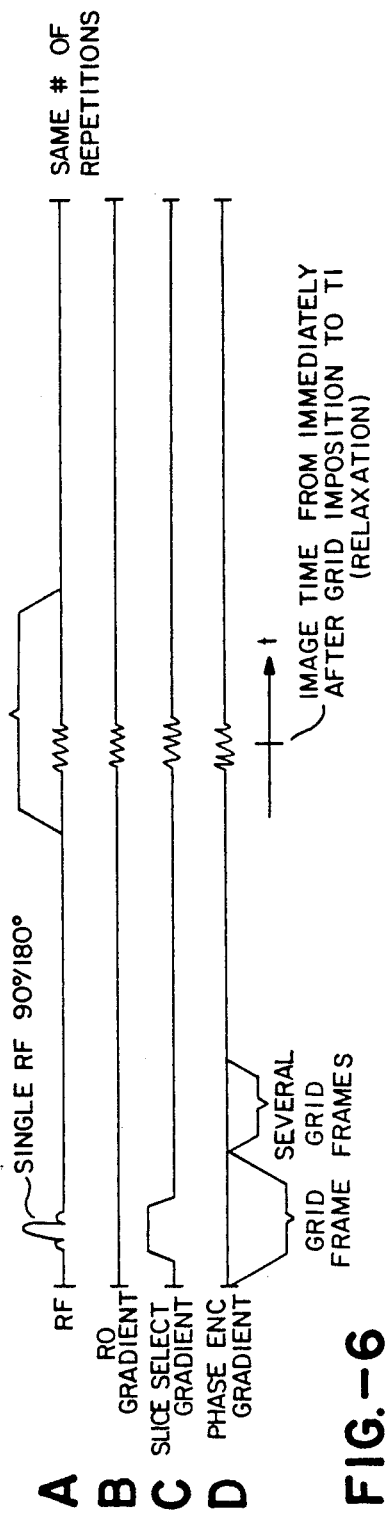
FIG.-5
FIG.-6

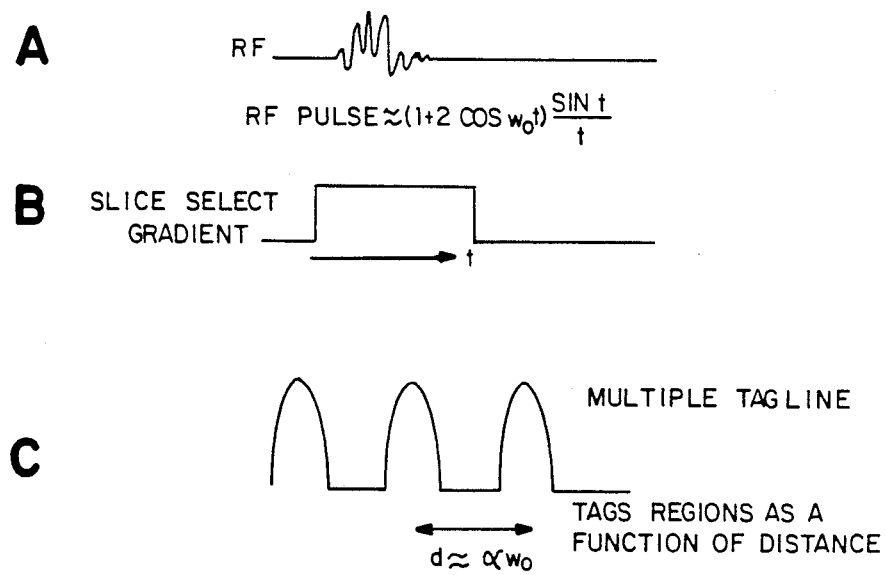
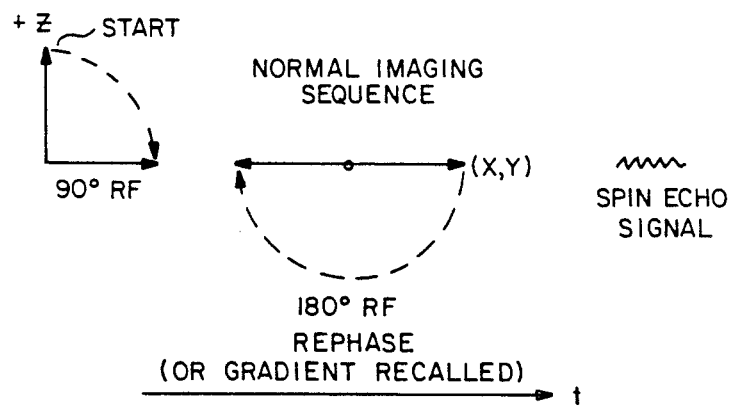
FIG.-7
FIG.-8A

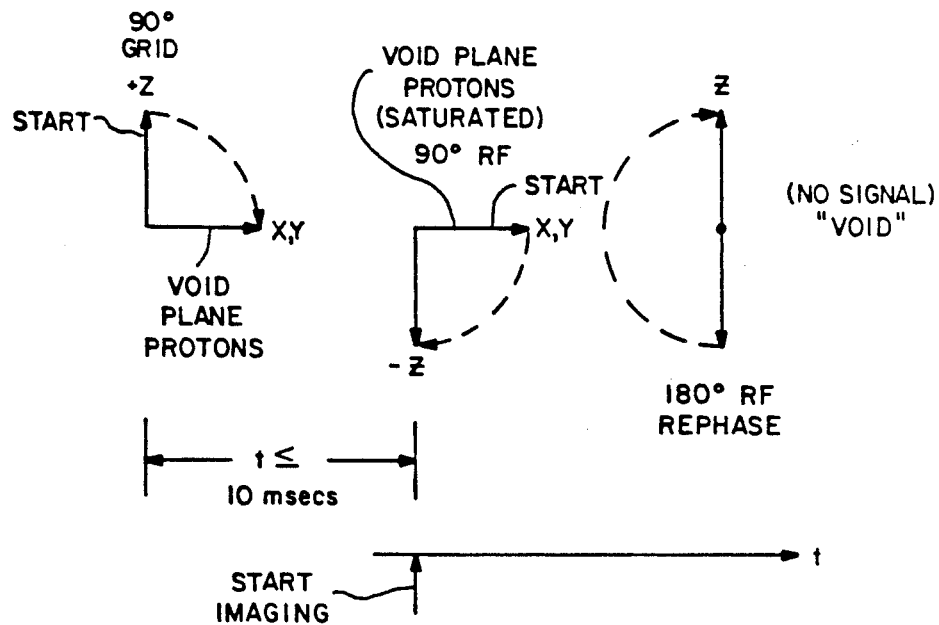
FIG. — 8B
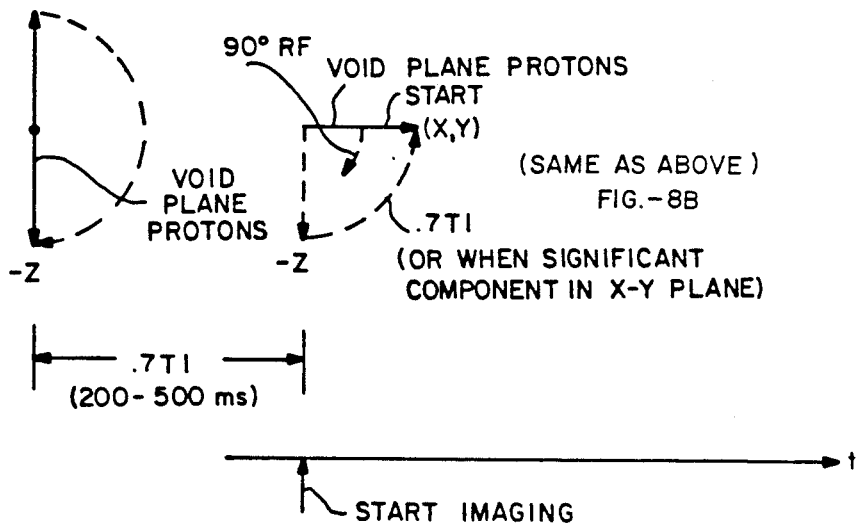
FIG. — 8C

MAGNETIC RESONANCE IMAGING METHOD

FIELD OF THE INVENTION

The present invention is directed to a magnetic resonance imaging method and more specifically, to a method of imaging the human heart to analyze its motion during the heartbeat.

BACKGROUND OF THE INVENTION

In classical magnetic resonance imaging (MRI) techniques, the proton density of physical tissue characteristics is sensed to discriminate between healthy and diseased tissue. In the case of tissue that is in motion, such as the human heart, diseased portion of the heart are optimally detected by assessment of wall motion of a heart chamber and wall thickness during this cardiac cycle. One technique which attempts to do the foregoing is the use of ultrasound (referred to as "echo" in the industry); and to some extent other techniques are X-ray computed tomography, contrast ventriculography, nuclear scanning, and finally classical or conventional MRI.

All these methods suffer from the same critical limitation: the inability to visualize and to track the same portion of the ventricular myocardium throughout the cardiac cycle. For instance, all tomographic imaging methods visualize a thick slice of space through which the myocardium moves during the cardiac cycle. Thus images taken at different instants in the heart cardiac cycle are actually different segments of the myocardium of the heart. The movement of the heart during the cardiac cycle is complex and involves displacement along all three axes.

One technique involving physical invasion of the heart itself to detect the foregoing has been to surgically implant markers. In addition to the invasiveness of the above technique, it does not adequately measure needed parameters.

MRI has been used for the measurement of blood flow in the human body but with limited success.

OBJECT AND SUMMARY OF INVENTION

It is a general object of this invention to provide an improved magnetic resonance imaging method.

In accordance with the above object, there is provided a magnetic resonance imaging method using a slice select gradient and where an image is produced by an imaging step including application of a radio frequency (RF) pulse or pulse sequence to a tissue specimen which produces signals utilized for forming said image. The method comprises the steps of manipulating the magnetic axis of selected protons in a slice to be selected by the slice select gradient in the imaging step to impose a grid line reference system on the slice, the manipulation causing the grid system to produce substantially no signals during a subsequent imaging step.

The manipulation includes the steps of utilizing at least one slice select gradient to excite selected protons in at least one predetermined void plane which forms a line of said grid system, and imposing an RF pulse on the excited protons with a predetermined power for a predetermined flip angle of the magnetic axes of said protons substantially to place such protons in a saturated condition during the later imaging step. Thereafter in the imaging step an image is taken of the specimen slice, the grid system in said slice producing substantially no signals.

BRIEF DESCRIPTION OF DRAWINGS

FIG. 3 is a view similar to FIG. 2 of a human heart but along the transverse axis of the heart utilizing a different type of reference grid format.

FIG. 4 is a representation of the human heart illustrating an alternative imaging method.

FIG. 4A is the representation of the actual image produced in conjunction with the method as illustrated in FIG. 4.

FIGS. 5A through 5E illustrate a normal MRI imaging sequence which is controlled or gated by a cardiac cycle.

FIGS. 6A through 6D show the foregoing standard imaging sequence in combination with the additional method of the present invention.

FIGS. 7A through 7C are waveform diagrams illustrating an alternative embodiment of the present invention.

FIGS. 8A through 8C are vector timing diagrams illustrating and explaining the method of the present invention.

DESCRIPTION OF THE PREFERRED EMBODIMENTS

Figure 1:
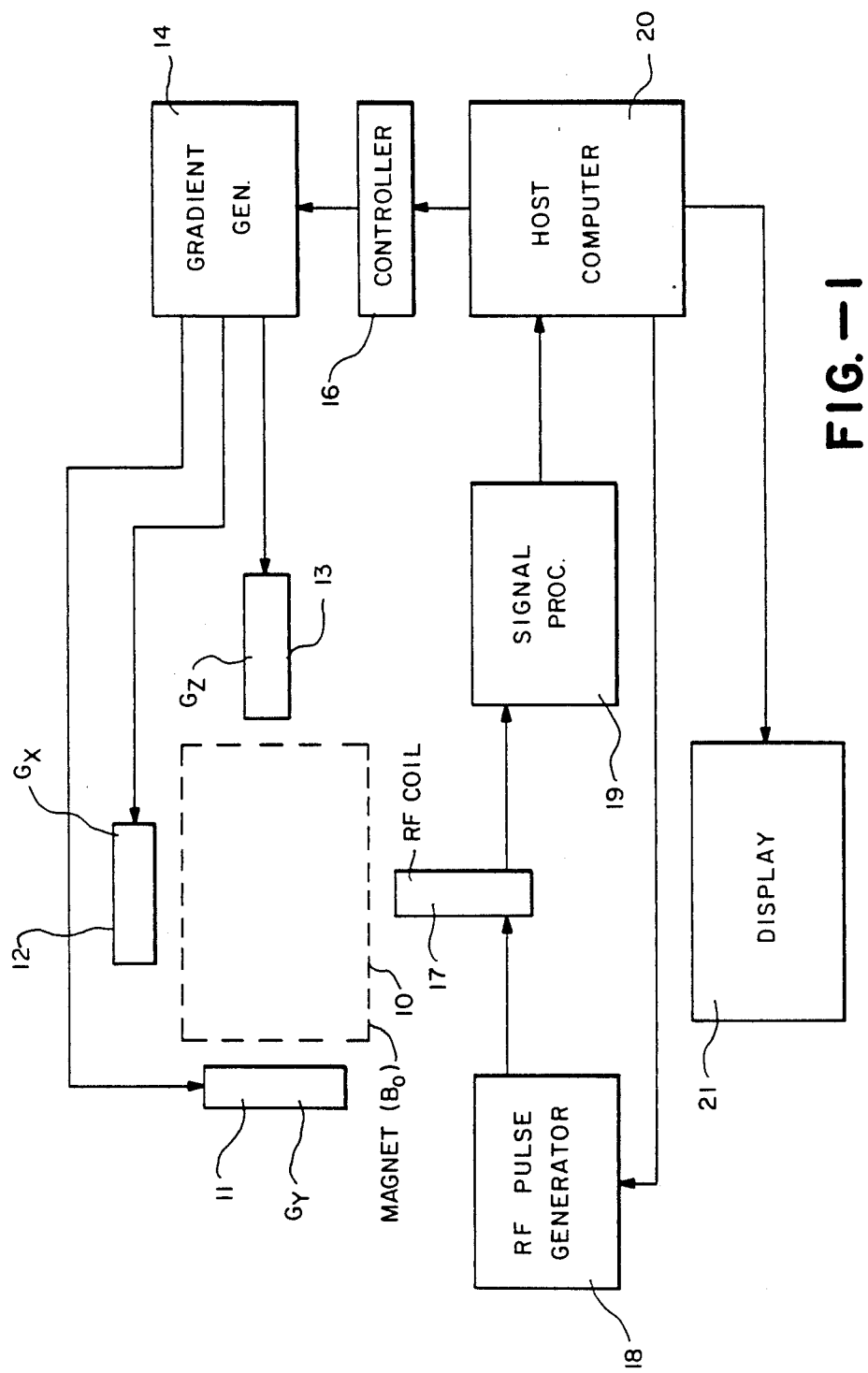
FIG. 1 is a block diagram of an MRI system utilizing the present invention.

The method of the present invention may be conveniently used with standard MRI apparatus if such apparatus has control capabilities where parameters may be easily varied. However, an ideal apparatus, as illustrated in FIG. 1 in broad format, is produced by the Resonex Corporation of Sunnyvale, Calif., with its basic imaging technique being shown in U.S. Pat. No. 4,743,851 "Apparatus and Method for Creating Non-Orthogonal Magnetic Resonance Imaging, " Ser. No. 089,941, filing date Aug. 25, 1987, in the names of Lim, Buonocore and Barratt, and assigned to Resonex Corp. The MRI apparatus shown in that application is ideally suited for the present method since it can be very easily controlled to provide image planes at any angle or offset.

In any case, referring to the generalized showing of an MRI device, as illustrated in FIG. 1, there is a main magnet 10 which provides a magnetic field $B_0$ which generates a steady magnetic field realizing a polarization of the nuclei of the protons of the specimen or subject for which an image is desired. Within magnet 10 there is a cavity or space in which the specimen or human to be examined is placed.

The apparatus also includes a gradient system for producing spatial linear field gradients. These gradient fields are conveniently established by a set of three orthogonal direct current coils 11, 12 and 13, which generate the three principal gradients $G_y$, $G_x$, and $G_z$. These coils are driven by gradient generator 14, which in turn is controlled by a controller 16 which communicates with the host computer 20. Typical gradients used in MRI image processing are the well known slice select, readout, and phase encoding gradients.

The third component of the typical MRI systems includes the radio frequency (RF) coil 17 which generates a radio frequency field in the specimen being analyzed and senses a free induction decay or spin echo signal which is generated after termination of the radio frequency pulse. RF pulse unit 18 excites RF coil 17.

The signal processor 19 receives the small microvoltage level spin echo signals which are reconstructed by computer 20 to form an image. Typically Fourier transform techniques are utilized. The image is digitized and stored in the memory section of computer 20 for later display on display unit 21.

FIGS. 5B through 5E illustrate a typical imaging sequence. In this specific situation imaging is triggered or gated from the cardiac waveform of a human heart, as shown in FIG. 5A.

In accordance with well known MRI imaging, the data acquisition sequence for a single slice, as illustrated in FIG. 5B, includes a 90° RF pulse (known as a flip angle), a later 180° RF (rephase) pulse and then the spin echo signal from the tissue is produced, as indicated. During these two RF pulses, FIG. 5C illustrates the imposition of a slice select gradient; FIG. 5D a readout gradient and FIG. 5E a phase encoding gradient in the proper time relationships. Each data acquisition frame or sequence for the slice may be done N number of times which is dependent on the number of rows and experiments in a slice or frame, for example, 128 by 4.

Figure 2:
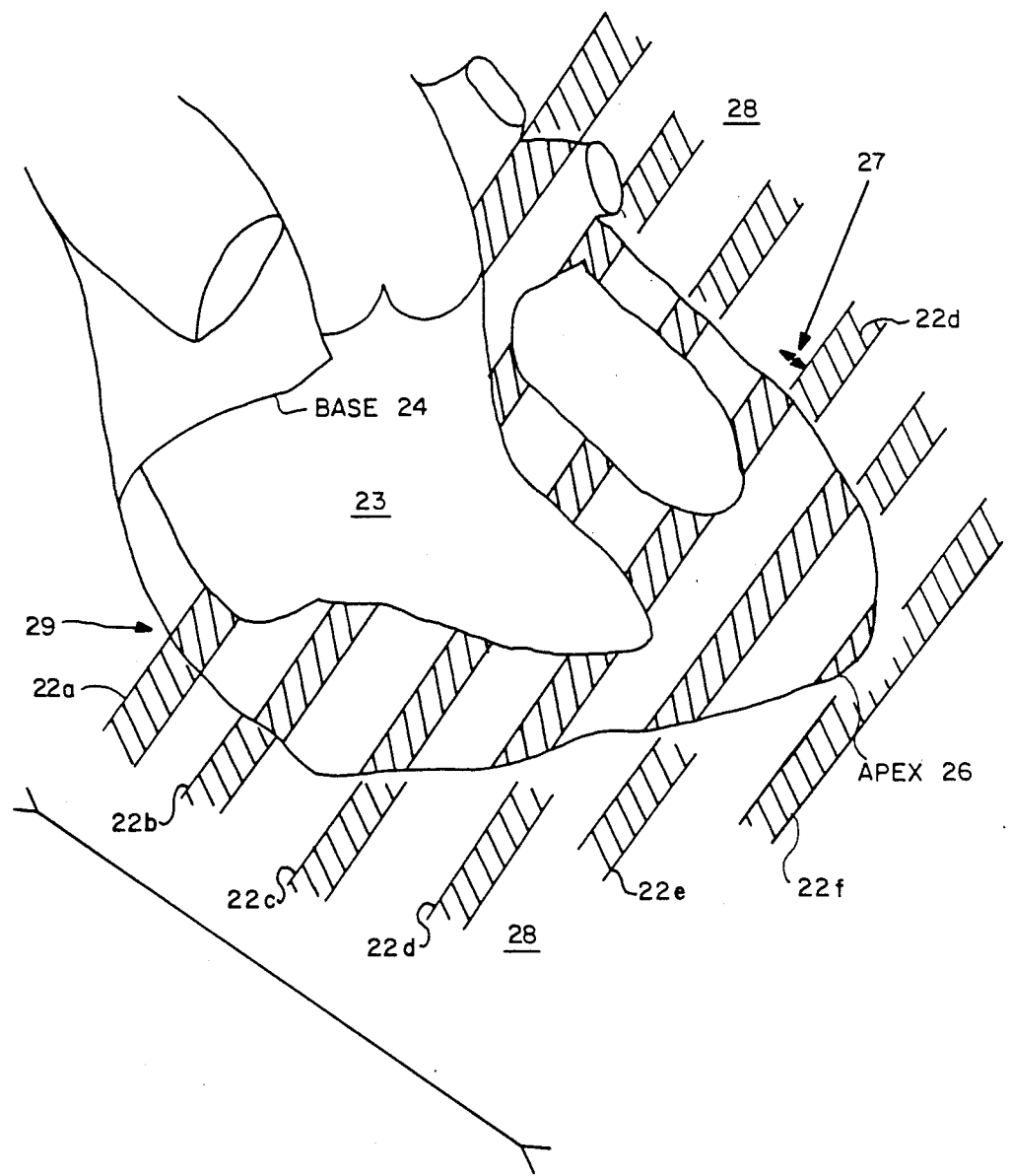
FIG. 2 is a representation of an image of the human heart along its longitudinal axis utilizing the method of the present invention.

In the method of the present invention before this standard imaging step is done, the selected protons in a slice to be imaged have imposed on them a grid line reference system, as illustrated, for example, in FIG. 2.

Specifically, the grid line reference in the embodiment of FIG. 2 is in the form of the cross-section of several void planes, shown as 22a through 22f. The heart 23 has a base 24 and an apex 26. The grid reference 22a–22f was imposed on the heart an earlier time relative to a later imaging step. Thus, information is contained here including what direction do the various muscles of the heart move as it beats, including how do individual pieces of the heart muscle contract and in what direction. For example, referring to the grid line 22d, the arrow indicated at 27 shows an offset in the line 22d caused by motion which occurred between the time the grid line reference was imposed and the imaging time. Generally speaking, the offset occurs between the heart itself and the chest wall, which is generally indicated at 28. Also, referring to the line 22f, the separation of a portion of the line at the apex 26 indicates that the apex 26 has moved toward the base 24. In comparison, line 22a at the point 29 shows very little relative movement, if any. Thus, the foregoing illustrates the advantages of the method of the present invention.

To summarize, the grid line system (22a–22f) is in effect "tagged" areas or planes of the heart tissue where in the MRI process the magnetic axis of the protons has been so manipulated that during the imaging step the grid reference produces no imaging signal or is in effect a "void." From a more general standpoint, there are disparate degrees of proton saturation between the grid line reference part of the tissue and the remaining tissue which does produce the normal, for example, spin echo signals. Due to the fact that the blood in the various cavities of the heart does not retain the grid line reference in the same manner as the tissue itself, these cavity portions are shown without the crossed hatching of the grid reference. Also, in fact, the so-called T1 relaxation time of various types of tissue may vary and thus the grid reference may reflect only a certain type of tissue.

Finally, with reference to the image of FIG. 2, its obvious that the image is taken perpendicular to the void planes 22a to 22f which, as will be discussed below in detail, are ideally imposed by means of simultaneous radio frequency (RF) pulses during a slice select gradient.

In addition to the use above in connection with cardiac performance where tissue is in motion, the present invention can also be used for labeling static tissue (or spins); for example, in radiation therapy port planning. A typical situation might be where radiation therapy is desired for a tumor which is on a portion of the liver. This organ is normally relatively static. In radiation therapy for such a tumor, a point or relatively small area where the tumor exists must be located on the liver in relation to the human body as a whole. For such radiation therapy, focused radiation beams are directed at the tumor from many different angular locations in order to achieve the desired radiation therapy. In the past primitive techniques such as felt pen markings on the bodies of the patient were utilized.

With the technique of the present invention, a suitable grid system can be imposed on the tumor. The grid system through successive images can indicate the three-dimensional extent of the tumor. Then, by suitable calibration between the coordinate systems for the magnetic resonance imaging machine and the radiation therapy device, the proper coordinates can be set up for the therapy device.

One way of implementing in detail the foregoing technique is to maintain the patient on the same stretcher or platform when transferred from the MRI device to the radiation therapy device. In fact, theoretically the platform could be located on a single track which was precisely constructed so that the patient is directly moved from the MRI-sensitive area to the radiation therapy area.

To tag or mark a void on a tumor area which is relatively small, a point-type mark is desired. This is easily achieved by providing three orthogonal void planes. Their common intersection is a point. And for that matter, for a line two void planes would determine such a line in space.

FIGS. 6A through 6D indicate the imposition of a grid by the provision of one or several parallel void planes. This might be referred to as "tagging" also. As indicated in FIGS. 6A through 6D, at 31 there is a later imaging sequence which is identical to that described in the same time axis as FIGS. 5A through 5D. However, before this imaging step is conducted, the void planes or grid reference are imposed by the following manipulation, as illustrated in FIG. 6A. Here, a single RF pulse (or simultaneously a group of several RF pulses) is imposed with flip angles which typically may be 90° or 180° or may range between those two angles. As illustrated in FIG. 6C, only the slice select gradient is used and this may be done several times for a single grid frame or several grid frames depending on application.

Referring to FIG. 1, the basic MRI system need only be slightly modified as, for example, the software control in host computer 20 since the tagging or grid imposition or manipulation step in FIGS. 6 is similar to an imaging step but in simplified form without an additional rephase 180° pulse; and also, of course, there is no spin echo signal to be received. Between the time of the grid imposition and the imaging time the power of the flip angle has been chosen so that the protons excited which form the grid will in effect be in a saturated condition during the later imaging step and therefore will produce no imaging signals (for example, the spin echo type).

The theoretical basis of the foregoing is illustrated more fully by the time vector diagrams in FIGS. 8A through 8C. First, FIG. 8A is a normal imaging sequence where, due to the main magnetic field $B_0$, as illustrated in FIG. 1, all magnetic axes of the protons of interest are lined up on a $+Z$ axis labelled "start." Then, in the standard imaging process, as implemented in FIG. 5B, the 90° RF pulse shifts the magnetic axes to the XY plane, as indicated in the next diagram, and then the 180° rephase RF (or gradient recall, depending on the imaging technique) shifts 180° in the negative portion of the XY plane. Thereafter, a spin echo signal is produced. Thus, from an MRI imaging standpoint, it should be kept in mind that a spin echo is only produced by a magnetic axis in the XY plane which occurs after the above sequence of imaging pulses.

Protons with their magnetic axis already in this plane are termed "saturated," as will be discussed below. If the imaging step is conducted with a magnetic axis of a proton already in this XY plane, then due to the 90/180° rephasing, the magnetic axes will be placed in the Z axis which produces no signal. The foregoing is illustrated in FIG. 8B where, referring to FIG. 6A, a 90° RF pulse has been applied before the imaging step indicated by the 90° grid reference and thus, the "start" from a $+Z$ axis produces void plane protons in the XY plane. If an imaging step is conducted immediately after the grid imposition (for example, substantially 10 milliseconds or less) the void protons still remain in the XY plane. Thus, this is labelled "start" in the second diagram, which is also the "start imaging" portion of the time axis, and a 90° RF pulse places the magnetic axes of these protons in a $-Z$ direction. Next the rephase 180° RF pulse places them in a $+Z$ direction and thus, since no spin echo signal is produced by such protons, this is a void.

With the grid generated by the technique of FIG. 8B, since the imaging is accomplished immediately after the imposition of the grid, the tissue has not moved significantly. Thus, this process may be useful for establishing an initial grid line pattern for later reference use with other parts of the process.

FIG. 8C illustrates the most utilitarian aspect of the invention where there is a time delay between the imposition of the grid plane or the "tagging" and the imaging so that, as illustrated in FIG. 2, the direction and amount of contraction or relaxation of the heart can be detected. Referring specifically to FIG. 8C, to accomplish the type of imaging as shown in FIG. 2, a 180° RF grid reference is first done before the imaging step, which places the selected void planes (selected by the slice select gradient) and shifts them from a $+Z$ to a $-Z$ direction. Then, typically, a time delay of 0.7 T1, with T1 the relaxation time of the heart tissue, is allowed. And as shown in the next diagram, this allows the magnetic axis of the tagged protons to move to the XY plane designated "start." Then, in the same manner as in the imaging step of FIG. 8B, the 90° RF pulse moves the excited protons back to the $-Z$ direction and the 180° RF pulse rephases to produce no signal or a void. It is obvious that the time delay 0.7 T1 may be modified and as long as there is a significant component in the XY plane during imaging, there will be a disparate signal difference between the grid reference portion of the tissue and the remainder.

Thus, in general, its obvious that the time delay between the imposition of a grid and the actual imaging may range anywhere from almost an immediate image to as long as T1. (T1 = the relaxation time.)

In partial summary, the essential element of the technique is that the resonant protons perturbed by the slice selective radio frequency pulse, in the presence of linear magnetic gradients, will retain memory of the RF excitation for a time dependent upon the longitudal magnetic relaxation time or T1 of the tissue of interest. If, before full recovery of magnetization in the RF perturbed areas, an MRI image of the tissue is obtained, there will be a signal difference between the "tagged" and "non-tagged" regions caused by the disparate degrees of proton saturation in the two areas. Intervening motion will be recorded as displacement and distortion of the RF tags.

As is apparent in FIG. 2, as has been partially discussed, its useful to simultaneously produce several parallel void planes. FIGS. 7A through 7C illustrate such a technique. This "multi-tag" capability utilizes a single specialized RF pulse, as shown in FIG. 7A, of the mathematical form as shown. Its a sine-cosine function of the modulated sinc type of the form $(1 = 2 \cos\omega_0 t) \sin t/\sqrt{t}$ where t is time and $\omega_0$ is the angular frequency. When this pulse has been mathematically manipulated by using a Fourier transform, as indicated in FIG. 7C this produces three radio frequency pulses which are simultaneous — one being a frequency shifted version of the adjacent. Thus, in accordance with well known MRI theory, since the slice select gradient provides in effect a changing potential gradient along the tissue of interest, each slice of the gradient will have a particular RF frequency which will resonate in accordance with the Larmour equation.

Rather than having a grid reference with parallel lines, a radial grid reference may be provided as shown in FIG. 3. Again, this is a short axis view of the heart shown at 40 with the left ventricle 41 and the right ventricle 42. The various tag lines or void planes are shown as 43a through 43d, with the chest wall being shown at 44 and the liver at 46. Here, as shown by the arrow 47, the grid reference provides a measurement of twist.

To produce the foregoing radial "tag" lines, the standard MRI system of FIG. 1 may be utilized. Initially, for each of the radial void planes, the angles theta, phi, omega and the offset distance are determined. Then, before the imaging step for each of the void planes 43a-43d desired, the slice select gradient is produced as indicated in FIG. 6C to select a slice at a predetermined angle with the RF frequency being chosen to produce a desired offset. The RF pulse power is adjusted to obtain the flip angle, typically of 180°, since the picture is to be taken later after the twist of the heart has been allowed to occur.

Although the void planes 43a through 43d are at different oblique angles, this is easily accommodated by the MRI system disclosed in the above patent.

The foregoing imaging or techniques of FIGS. 2 and 3 might be termed "in-plane images" since they are in a plane orthogonal to the void or tagging planes. Although this type of imaging permits accurate depiction of motion within the plane of imaging, it does not ensure that the motion intersecting the imaging plane may be sensed. In other words, this might be termed a "through" plane motion. To sense this type of three dimensional motion the technique as illustrated in FIGS. 4 and 4A is utilized. Here there are void planes 51 and 52 which are formed by appropriate slice select gradients and these void planes are imposed or sandwiched around the region to be imaged indicated at 53. However, the imaging slice 54 is larger than the width of region 53, as will be discussed below.

In effect, referring briefly to FIG. 4A, the actual image produced is actually parallel to the void planes 51 and 52, as opposed to the perpendicular orientation shown in FIGS. 2 and 3. After the void planes have been formed, the imaging step is conducted at, for example, a 0.7 T1 time, by selecting the slice 54 which is greater than the width of the imaged region 53. Keeping in mind that the specimen may have moved or distorted relative to the imaged region 53, this original region 53 will still be produced. In other words, all parts of the original sandwiched region 53 will be imaged including those portions which may have moved into the void planes. Thus, tracking of the distorted tissue in a through plane direction is allowed exclusive of contamination by adjacent regions. By proper timing or gating of the images relative to the cardiac cycle, successive images and tagging can be accomplished to show a sequence of movement. Thus, an improved MRI imaging method has been provided.

We claim:

1. A magnetic resonance imaging (MRI) method to track the motion of tissue where an image is produced by application of a radio frequency (RF) pulse sequence to a tissue specimen which produces signals utilized for forming said image, the method comprising the following steps:

at least partially saturating protons in at least one plane by applying a slice select gradient and at least one RF pulse to impose a grid system in the tissue specimen each of said, at least one saturated plane forming a saturated line of said grid system, the saturation causing said grid system to produce substantially no said signals during a subsequent imaging step;

delaying a variable period of time less than the T1 relaxation time of said tissue specimen to allow the tissue specimen of interest to move; following said delay producing an image of the tissue specimen, said image being taken perpendicular to said at least one said saturated plane whereby motion of the tissue specimen between the saturation and imaging steps is reflected in distortion and/or translation of said saturated line as seen in the image.

2. A method as in claim 1 where a plurality of said saturated planes spaced from one another are imposed simultaneously.

3. A method as in claim 2 where said saturated planes are simultaneously produced by application of one RF pulse where said RF pulse is of the form $$RF(t) = (1 + 2 \cos\omega_0 t) \sin t / \sqrt{t}$$

wherein t is time, RF is the RF pulse, and $\omega_0$ is the angular frequency determining the spacing between said planes.

4. A method as in claim 1 wherein said tissue specimen is a human or animal heart having a known cardiac cycle and wherein said grid system is imposed on said heart at any desired predetermined time in said cardiac cycle and said imaging step is done at any later time in said cardiac cycle but less than said T1 time, the purpose of said saturation and imaging being to measure the motion of the heart tissue between the time that the grid is imposed and the time of imaging.

5. A method as in claim 1 where said imaging step is done as soon as possible without substantial time delay after said grid system has been imposed, said time being of the order of 10 milliseconds, whereby the location of the grid system is effectively seen before any motion has taken place.

6. A method as in claim 5 where a flip angle produced by said at least one RF pulse during the saturation step is 90° so as to optimize the darkness of each saturated line in said imaging step which closely follows said imposition of said grid system where darkness is the relative intensity between the saturated region and the unsaturated region, 7. A method as in claim 1 where said imaging step is done after a substantial delay following said saturation step, the delay being on the order of and not greater than the T1 relaxation time of said tissue specimen.

8. A method as in claim 7 where because of said substantial delay between said saturation step and said imaging step the RF flip angle in said saturation is approximately 180°.

9. A magnetic resonance imaging (MRI) method where an image is produced by application of a radio frequency (RF) pulse sequence to a tissue specimen which produces signals utilized for forming said image, the method comprising the following steps:

at least partially saturating protons in at least one plane by applying a slice select gradient and at least one RF pulse to impose a grid system in the tissue specimen, each of said at least one saturated plane forming a saturated line of said grid system, the saturation causing said grid system to produce substantially no said signals during a subsequent imaging step;

producing an image of said grid system in the tissue specimen;

and utilizing said grid system for radiation therapy port planning.

* * * * *